US007686836B2

(12) United States Patent
Johnston et al.

(10) Patent No.: US 7,686,836 B2
(45) Date of Patent: Mar. 30, 2010

(54) BONE DISTRACTOR AND METHOD

(75) Inventors: Thomas S. Johnston, Jacksonville, FL (US); Shawn Burke, Jacksonville, FL (US)

(73) Assignee: KLS-Martin, L.P., Jacksonville, FL (US)

( * ) Notice: Subject to any disclaimer, the term of this patent is extended or adjusted under 35 U.S.C. 154(b) by 448 days.

(21) Appl. No.: 11/128,595

(22) Filed: May 13, 2005

(65) Prior Publication Data

US 2005/0256526 A1    Nov. 17, 2005

Related U.S. Application Data

(60) Provisional application No. 60/570,657, filed on May 13, 2004.

(51) Int. Cl.
*A61B 17/66* (2006.01)
(52) U.S. Cl. .......................... 606/282; 606/71
(58) Field of Classification Search .................. 606/60, 606/69, 70, 71, 90, 105, 53, 57, 280–286
See application file for complete search history.

(56) References Cited

U.S. PATENT DOCUMENTS

| 2,434,431 | A |   | 1/1948  | Pincock |  |
|---|---|---|---|---|---|
| 3,547,113 | A |   | 12/1970 | Swanson |  |
| 4,872,449 | A |   | 10/1989 | Beeuwkes, III |  |
| 4,929,247 | A |   | 5/1990  | Rayhack |  |
| 5,147,358 | A |   | 9/1992  | Remmler |  |
| 5,364,396 | A |   | 11/1994 | Robinson et al. |  |
| 5,807,382 | A | * | 9/1998  | Chin ........................... 606/53 |
| 5,810,812 | A |   | 9/1998  | Chin |
| 5,842,856 | A |   | 12/1998 | Casey |
| 5,855,580 | A | * | 1/1999  | Kreidler et al. ................ 606/71 |
| 5,902,304 | A | * | 5/1999  | Walker et al. .................. 606/71 |
| 6,355,036 | B1 | * | 3/2002 | Nakajima ...................... 606/57 |
| 6,423,069 | B1 |   | 7/2002 | Sellers |
| 6,471,706 | B1 | * | 10/2002 | Schumacher et al. .......... 606/69 |
| 6,786,910 | B2 | * | 9/2004 | Cohen et al. ................... 606/71 |
| 6,908,469 | B2 | * | 6/2005 | Sellers et al. ................ 606/105 |
| 2002/0035368 | A1 |   | 3/2002 | Schumacher |
| 2003/0105463 | A1 | * | 6/2003 | Wolgen ......................... 606/71 |
| 2005/0119659 | A1 | * | 6/2005 | Pfefferle et al. ................ 606/71 |

OTHER PUBLICATIONS

Li, Kasey K, MD,DDS, et al., Distraction Osteogenesis in Adult Obstructive Sleep Apnea Surgery: A Preliminary Report, pp. 6-10.
Molina, Fernando, et al., Simultaneous Maxillomandibular Distraction, pp. 206-212.

* cited by examiner

*Primary Examiner*—Thomas C Barrett
*Assistant Examiner*—Michael J Araj
(74) *Attorney, Agent, or Firm*—Thomas C. Saitta

(57) ABSTRACT

A bone distractor having four bone plate attachment members for affixation to the posterior and anterior maxilla and/or zygomatic buttress and to the posterior and anterior mandible, the attachment members mounted onto a pair of parallel rods, one rod being a threaded drive rod and the other being a releasable guide rod, whereby rotation of the drive rod causes dimensional separation of the anterior attachment members from the posterior attachment members. The guide rod can be quickly removed such the superior attachment members joined to the maxilla and/or zygomatic buttress are physically separated from the inferior attachment members joined to the mandible such that the jaw can be opened.

31 Claims, 7 Drawing Sheets

BONE DISTRACTOR AND METHOD

This application claims the benefit of U.S. Provisional Patent Application Ser. No. 60/570,657, filed May 13, 2004.

BACKGROUND OF THE INVENTION

This invention relates generally to the field of medical compression and distraction devices in the field of bone fixation, repair and regeneration, and more particularly relates to such devices and methods utilized in mandibular and maxillary craniofacial repair, facial reconstruction, and treatment for congenital, developmental and traumatic defects.

It is often desirable or necessary to effect reconstruction or repair of the craniofacial bones defining the face of a person, such as the midface, the mandible and/or the maxilla. This need may arise from congenital conditions, developmental disorders or trauma. In many circumstances the abnormalities are corrected by first dividing a bone through osteotomy, i.e., cutting or fracturing a bone to create two segments separated by a gap or space. In some instances the bone segments will be shifted into the proper orientation and alignment, and then fixed in place relative to each other until bone growth across the gap results in the formation of a unitary bone member. In other instances it is necessary to lengthen the original bone member, in which case devices known as distractors are utilized. A distractor is a device that has affixation means, such as bone plates, that are joined to each of the bone segments on opposite sides of the osteotomy. The device further includes distraction means that allows the distance between the bone plates to be slowly increased over time, thereby allowing new bone growth to occur between the bone segments. The new bone growth increases in dimension until the proper bone length is achieved, at which time the distraction process is halted and the distractor is removed.

A typical example of this procedure is when the mandible or jawbone fails to fully develop in the anterior-posterior direction, a condition known as mandibular hypoplasia, which is manifested as a severely fore-shortened chin. To correct this anomaly, osteotomies are performed on each side of the mandible and a pair of distraction devices are affixed to the mandible. Extension of the distractors is performed in unison to lengthen the mandible until the desired position of the mandible relative to the midface is achieved. After sufficient regeneration and healing, the distractors are removed.

For another example, it is often desired to advance the midface or maxillary region relative to the jaw and skull to correct for maxillary hypoplasia, where the upper lip and/or nose are depressed relative to the remainder of the face structure. In this case the osteotomy may be performed across the maxilla to the nasal cavity, and a pair of distractors are affixed across the osteotomy gap, or an external distraction apparatus is mounted to the skull with affixed means to distract the anterior maxillary segment. Gradual extension of the distractors in unison advances the anterior maxillary segment relative to the posterior maxillary segments while bone regeneration fills in the osteotomy gap. When the proper position is achieved, distraction is halted. After sufficient regeneration and healing, the distractors are removed.

In certain situations it is necessary to advance both the mandible and the maxilla simultaneously to address the facial anomaly. To achieve this, osteotomies are performed on both the mandible and the maxilla, such that the anterior portions of the mandible and the maxilla are separated from the posterior portions. In one approach, four independent distractors are then affixed across the osteotomies, two on the maxillary segments and two on the mandibular segments. Distraction is performed as set forth above until the proper positions are reached for the mandible and the maxilla, and the distraction devices are removed after sufficient regeneration and healing. Alternatively, the upper and lower teeth can be wired together and a pair of distractors mounted to the mandible, such that advancement of the distractors simultaneously distracts both the anterior portion of the mandible and the anterior portion of the maxilla.

The known protocols for distraction of the mandible and maxilla possesses inherent problems. Affixation of the distractors involves invasive surgery, with multiple incisions and implantations of bone screws to affix the distractor bone plates being required. Thus, it is desirable to reduce the number of invasive procedures that must be done to address the craniofacial anomalies. It is often necessary to wire together or otherwise join the mandible to the maxilla such that normal opening of the jaw is precluded during the course of the treatment. This increases the risk of asphyxiation or choking, and thus it is desirable to provide a methodology and apparatus wherein the mandible can be quickly released from the maxilla if necessary.

It is an object of this invention to provide a craniofacial distraction device and method that addresses the problems set forth above in circumstances where simultaneous distraction of both the mandible and the maxilla are required. It is an object of this invention to provide a distractor device that may be affixed to both the mandible and the maxilla such that the anterior mandibular and maxillary segments are advanced simultaneously. It is an object of this invention to provide a distractor device that may be utilized in paired configuration, whereby only two distractors are necessary to achieve distraction of both sides of the mandible and maxilla, without need to wire together the upper and lower teeth. It is an object of this invention to provide a distractor device that may be converted to use as a single distractor, such that the device is adaptable for use with either the mandible or the maxilla. It is an object of this invention to provide a distractor device that provides a means for quick release of the superior components from the inferior components, whereby the release does not require damage or destruction of the distractor device such that the mandible can be freed from the maxilla and subsequently reunited. These objects as set forth above will be met as provided for in the disclosure to follow, and other objects not expressly set forth at this time will become apparent upon review of the disclosure to follow.

SUMMARY OF THE INVENTION

The invention is a bone distractor and its method of use, and is especially drawn to a bone distractor used in mandibular and maxillary craniofacial repair, reconstruction and treatment that enables a surgeon to simultaneously lengthen the maxilla and the mandible. In a representative illustration, osteotomies are provided on the left and right sides of the mandible and the maxilla, such that the anterior portions of the mandible and the maxilla are divided from the posterior portions. A pair of distractors is utilized, with one distractor affixed to each side of the skeletal structure.

The bone distractor of the invention comprises a means for attachment to the posterior portion of the mandible, a means for attachment to the anterior portion of the mandible, a means for attachment to the posterior portion of the maxilla and/or the zygomatic buttress and a means for attachment to the anterior portion of the maxilla, all of which comprise bone plates affixed by bone screws, or similar bone attachment members known in the art. The bone distractor further comprises distraction means to lengthen the device as required, such that the anterior portion of the mandible and the anterior portion of the maxilla are gradually separated from the posterior portions of the mandible and maxilla, and release means to allow the attachment members affixed to the mandible to be quickly released from the members attached to the maxilla and/or zygomatic buttress so that the jaw may be opened and the interior of the mouth and the throat may be accessed if necessary.

The distractor further comprises a pair of pin, shafts or rod members disposed in parallel manner between a drive rod retainer member and a bridging member, one rod member being a rotatable drive rod member threaded over the major portion of its length, and the other being a releasable guide rod member threaded only on one end. The posterior attachment means are connected to each other by the drive rod retainer member, with one posterior attachment means preferably being mounted onto the threaded drive rod by swivel means. The anterior attachment means are connected to each other by the bridging member. The bridging member has a threaded sleeve to receive the threaded drive rod, whereby rotation of the threaded drive rod causes the bridging member and the anterior attachment means to separate linearly from the drive rod retainer member and the posterior attachment means.

The superior bone attachment means attached to the maxilla and/or the zygomatic buttress comprise bone plates having knuckle ring members that mate with similar members on the drive rod retainer member and the bridging member, with the releasable guide rod member extending through these knuckle ring members. The posterior end of the releasable guide rod member is threaded and received within an internally threaded knuckle ring member on the drive rod retainer member, whereby the releasable guide rod member may be unthreaded and completely removed from all the knuckle ring members, thereby releasing the bone plates attached to the maxilla and/or zygomatic buttress from the drive rod retainer member and the bridging member, and thus from the bone plates attached to the mandible.

DETAILED DESCRIPTION OF THE INVENTION

Figure 1:
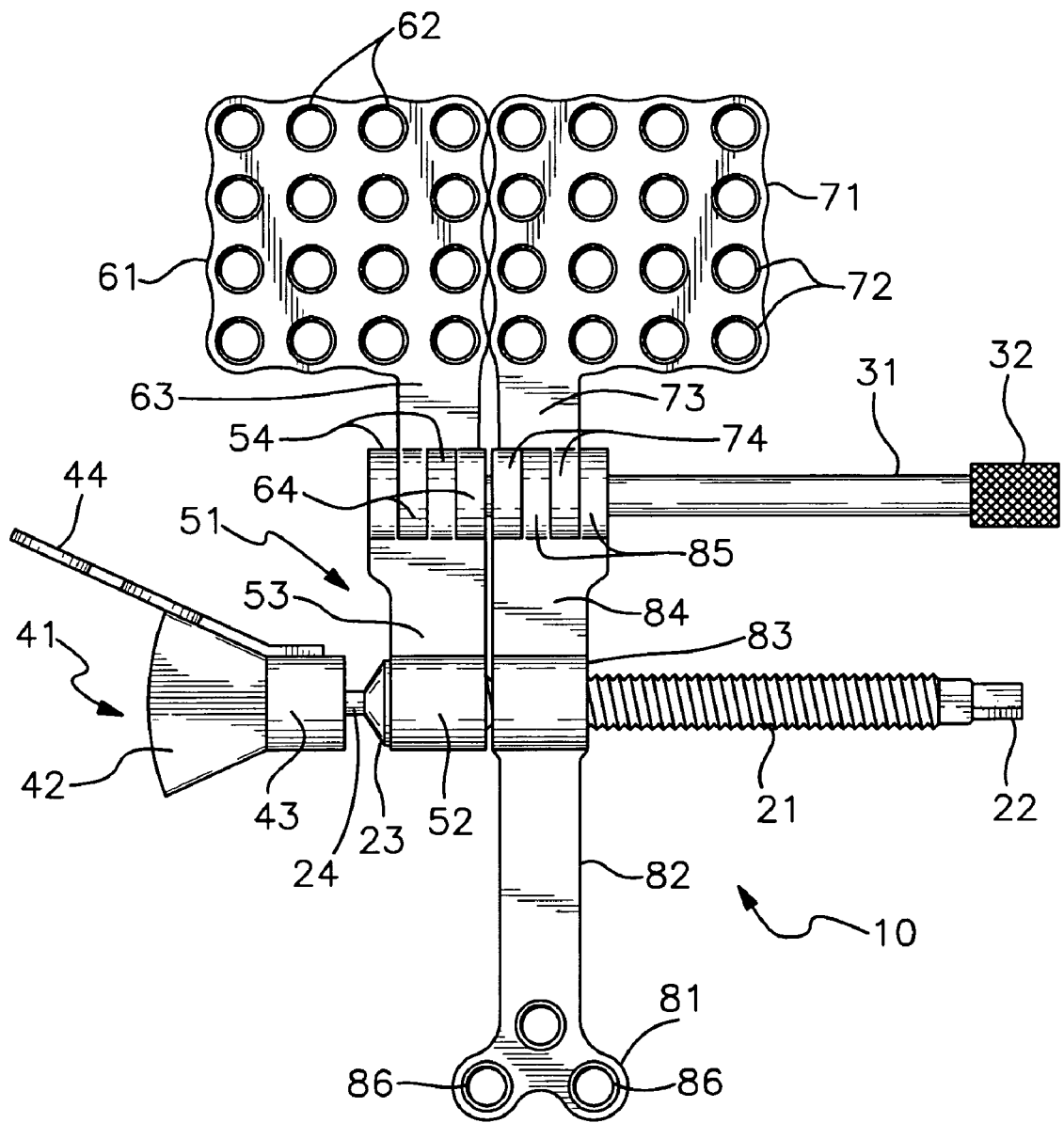
FIG. 1 is a plan view of the invention shown in the non-expanded configuration.

With reference to the drawings, the invention will now be described in detail with regard for the best mode and the preferred embodiment.

The invention is a bone distractor and its method of use, and is especially drawn to a bone distractor used in mandibular and maxillary craniofacial repair, reconstruction and treatment that enables a surgeon to simultaneously lengthen the maxilla and mandible with a single distractor. In a representative procedure, osteotomies are provided on the left and right sides of the mandible and the maxilla, such that the anterior portion of the mandible and the anterior portion of the maxilla are divided from the posterior portions of the mandible and the maxilla. In this case a pair of distractors is utilized, with one distractor affixed to the left side of the skeletal structure and the other distractor affixed to the right side.

The bone distractor 10 of the invention comprises posterior mandible attachment means 20 for attaching the device 10 to the posterior portion of the mandible 101 or ramus 103, and anterior mandible attachment means 30 for attaching the device 10 to the anterior portion of the mandible 101, with the inferior osteotomy 105 disposed between the posterior mandible attachment means 20 and the anterior mandible attachment means 30. The bone distractor 10 further comprises posterior maxilla attachment means 40 for attaching the device 10 to the posterior portion of the maxilla 102 and/or the zygomatic buttress 104, and anterior maxilla attachment means 50 for attachment to the anterior portion of the maxilla 102, with the inferior osteotomy 105 disposed between the posterior maxilla attachment means 40 and the anterior maxilla attachment means 50. The attachment means 20, 30, 40 and 50 comprise apertured bone plates or any similar attachment members known in the art that accomplish the goal of securing the device to the various bone segments. The bone distractor 10 further comprises distraction means 60 that lengthens the device as required, such that the separation distance between the anterior attachment means 30, 50 and the posterior attachment means 20, 40 is increased in a controlled manner, and release means 70 that allows the inferior attachment means 20 and 30 attached to the mandible 101 to be quickly released from the superior attachment means 40 and 50 attached to the maxilla 102 and/or the zygomatic buttress 104, such that the jaw can be opened and the interior of the mouth and the throat may be accessed if necessary. For simplicity in this disclosure, reference hereafter to the posterior portion of the mandible 101 shall be understood to include the ramus 103 and reference hereafter o the posterior portion of the maxilla 102 shall be understood to include the zygomatic buttress 104.

The distractor 10 has a pair of rod members 21 and 31 disposed in parallel manner in a fixed spatial relationship between a drive rod retainer member 51 and a bridging plate member 84, one rod member being a rotatable, threaded drive rod member 21 and the other being a releasable guide rod member 31. The posterior mandible attachment means 20 and the posterior maxilla attachment means 40 are connected to each other by the drive rod retainer member 51, with the posterior mandible attachment means 20 preferably being mounted onto the threaded drive rod 21 by swivel means 80. The anterior mandible attachment means 30 and the anterior maxilla attachment means 50 are connected to each other by the bridging plate member 84.

Figure 2:
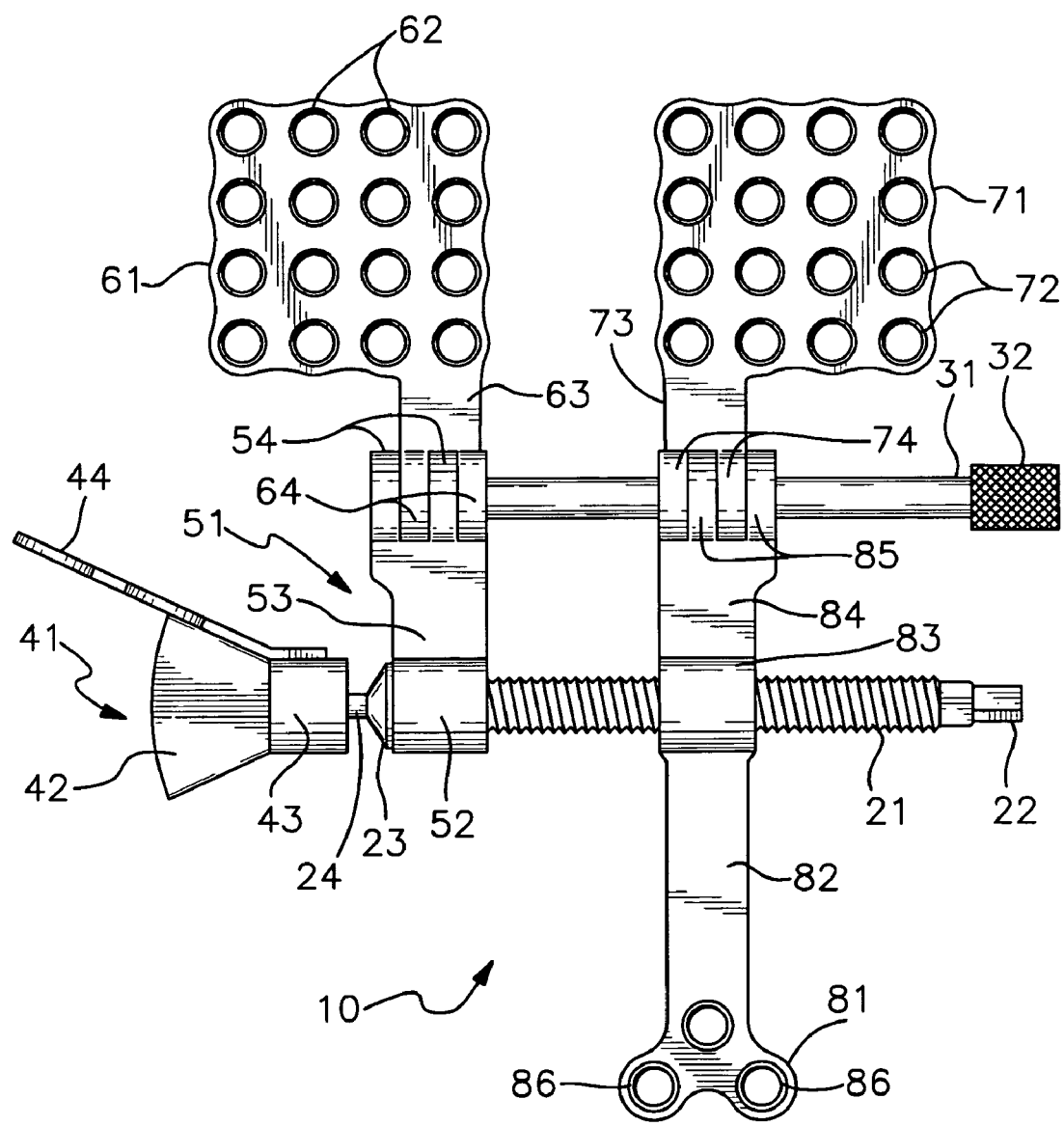
FIG. 2 is a plan view of the invention similar to FIG. 1 with the invention shown in an expanded configuration.

The drive rod retainer member 51 has a non-threaded sleeve member 52 that receives the posterior end of the drive rod member 21, such that rotation of the drive rod member 21 does not result in any engagement with the sleeve member 52. The bridging plate member 84 has an internally threaded sleeve 83 to receive the threaded drive rod 21, whereby rotation of the threaded drive rod 21 causes the bridging plate member 84, the anterior mandible attachment means 30 and the anterior maxilla attachment means 50 to separate linearly from the drive rod retainer member 51, posterior mandible attachment means 20 and the posterior maxilla attachment means 40, as shown in FIG. 2. In the embodiments as shown, the threaded drive rod 21 is disposed inferiorly to the guide rod member 31, but it is to be understood that these elements could be reversed with corresponding reversal of complementary components that receive these elements.

Figure 3:
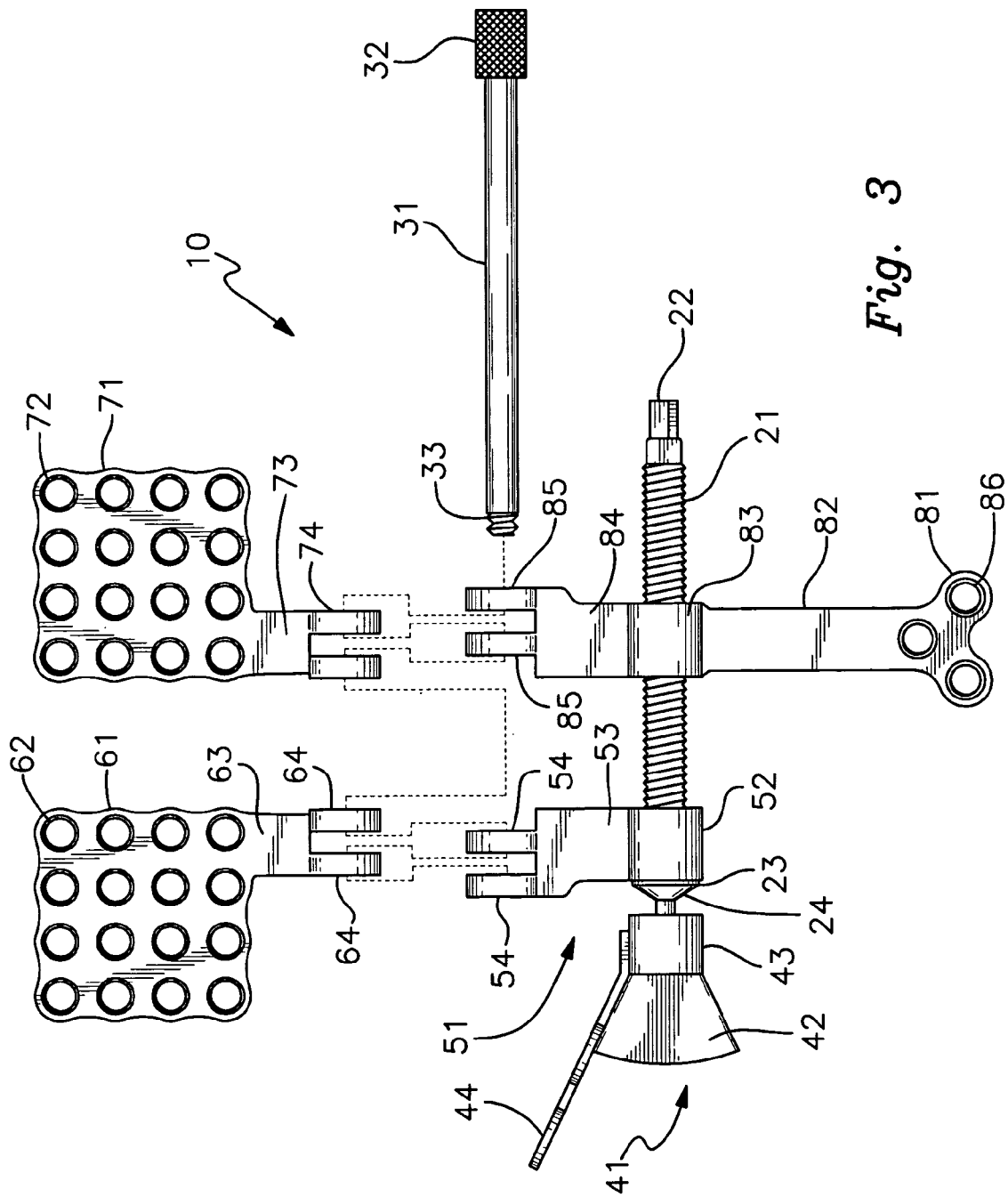
FIG. 3 is an expanded view of the invention showing the releasable guide rod and two superior bone attachment plate members separated from the inferior components of the invention to allow the jaw to be opened or to allow the inferior components to be utilized as a single distractor device.
Figure 4:
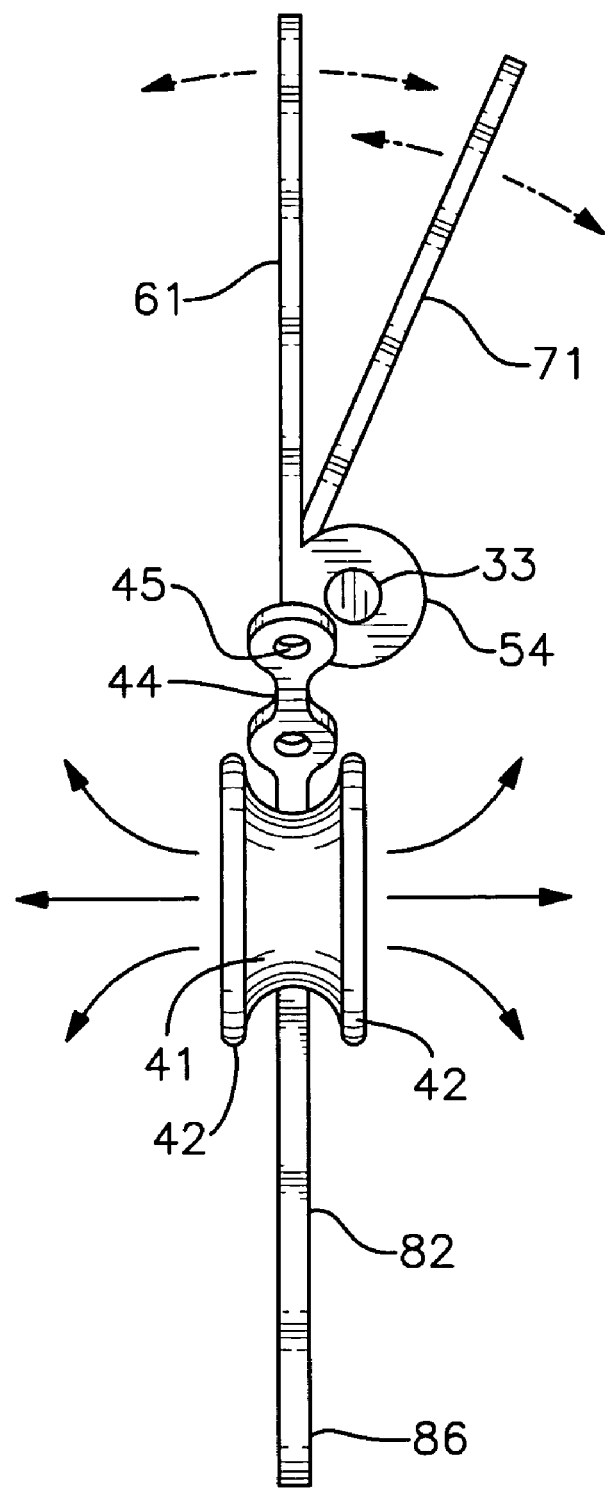
FIG. 4 is an anterior view of the invention showing the posterior superior bone attachment plate member pivoted out of plane from the anterior superior bone attachment plate member.
Figure 5:
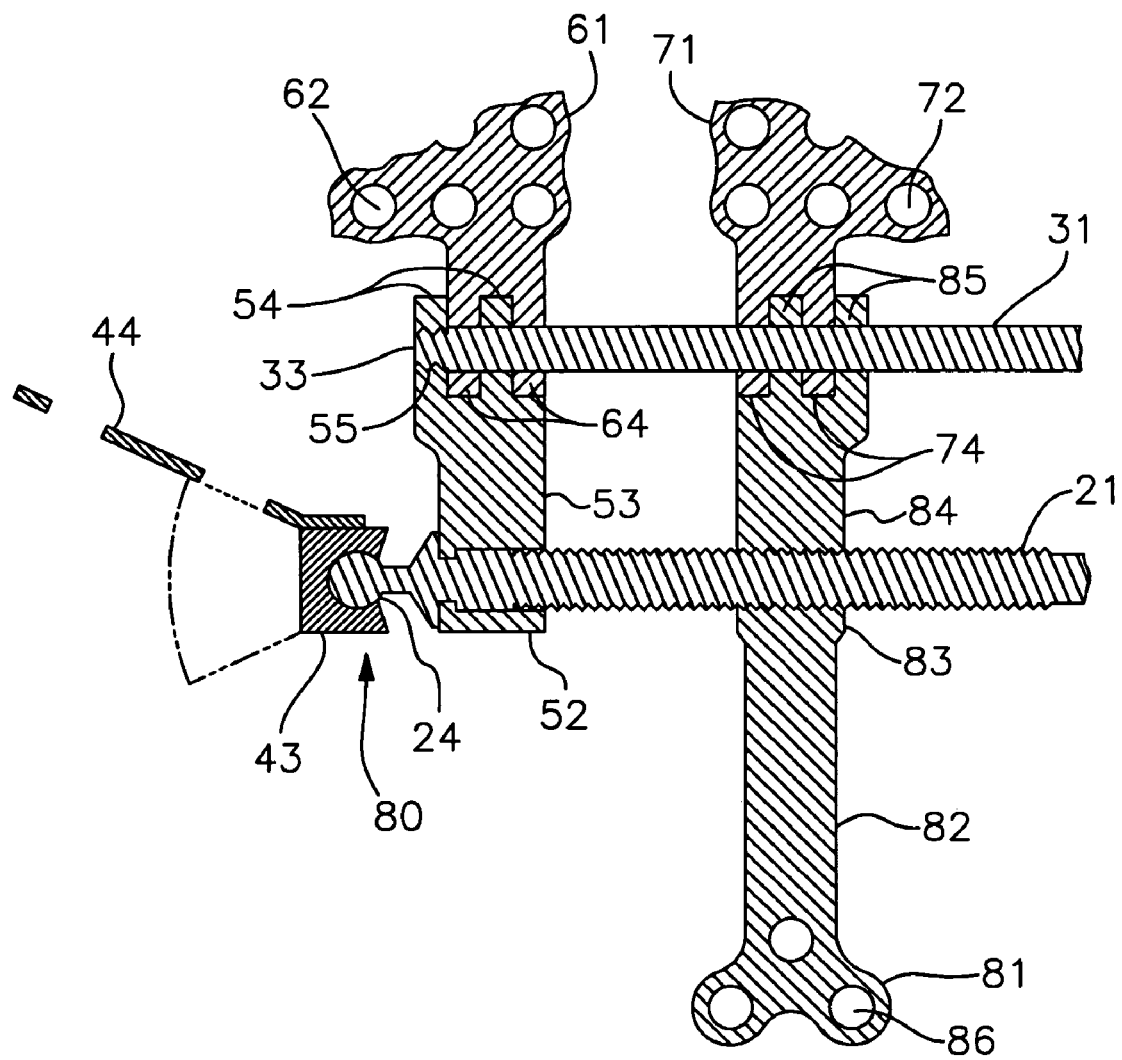
FIG. 5 is a partial cross-section view of all components of the invention taken along multiple parallel planes so as to pass through the longitudinal axis of the releasable guide rod member and the longitudinal axis of the rotatable threaded drive rod member.
Figure 6:
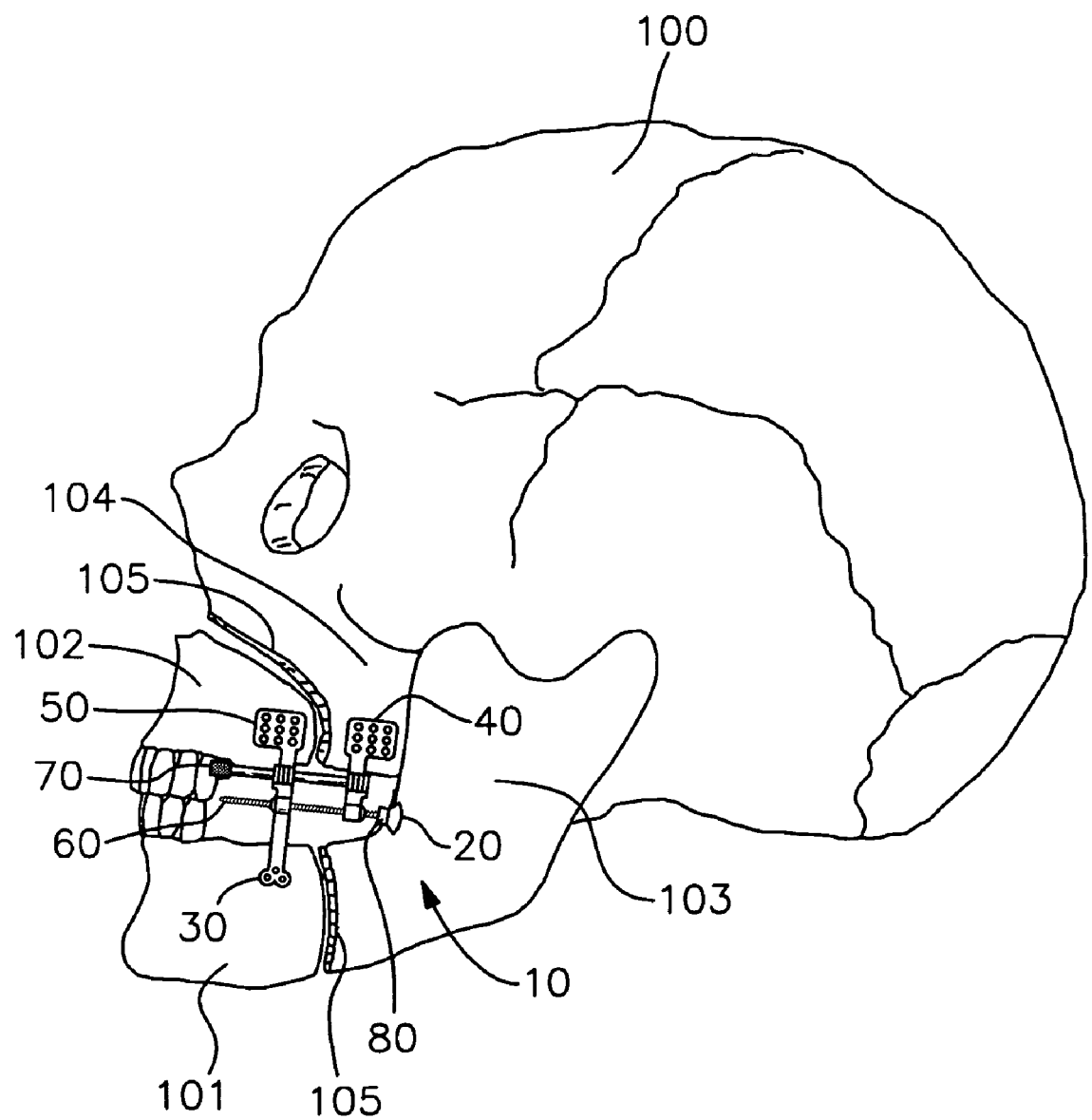
FIG. 6 is an illustration of the invention as affixed to a skull in order to provide distraction about osteotomies in the maxilla and mandible.

The attachment means 40 and 50 attached to the anterior and posterior segments of the maxilla 102 preferably comprise bone plates 61 and 71 having apertures 62 and 72 to receive fastener elements. Bone plate 61 further comprises knuckle ring members 64 disposed on an arm member 63, and bone plate 71 further comprises knuckle ring members 74 disposed on an arm member 73. the knuckle ring members 64 and 74 mate with complementary knuckle ring members 54 on the drive rod retainer member 51 and knuckle ring members 85 on the bridge plate member 84, with the releasable guide rod member 31 extending through the bores defined by these axially aligned sets of knuckle ring members 54, 64, 74 and 85, in a manner that allows the maxilla attachment means 40 and 50 to be pivoted relative to the releasable guide rod member 31. The posterior end 33 of the releasable guide rod member 31 is threaded over a short distance and is received within an internally threaded knuckle ring member 54 on the drive rod retainer member 51, whereby the releasable guide rod member 31 may be unthreaded and completely removed from the knuckle ring members 54, 64, 74 and 85, thereby releasing the bone plates 61 and 71 attached to the anterior and posterior segments of the maxilla 102 from the drive rod retainer member 51 and the bridging plate member 84, and thus from the attachment means 20 and 30 attached to the anterior and posterior segments of the mandible 101, as shown in FIG. 3 and FIG 6.

Figure 7:
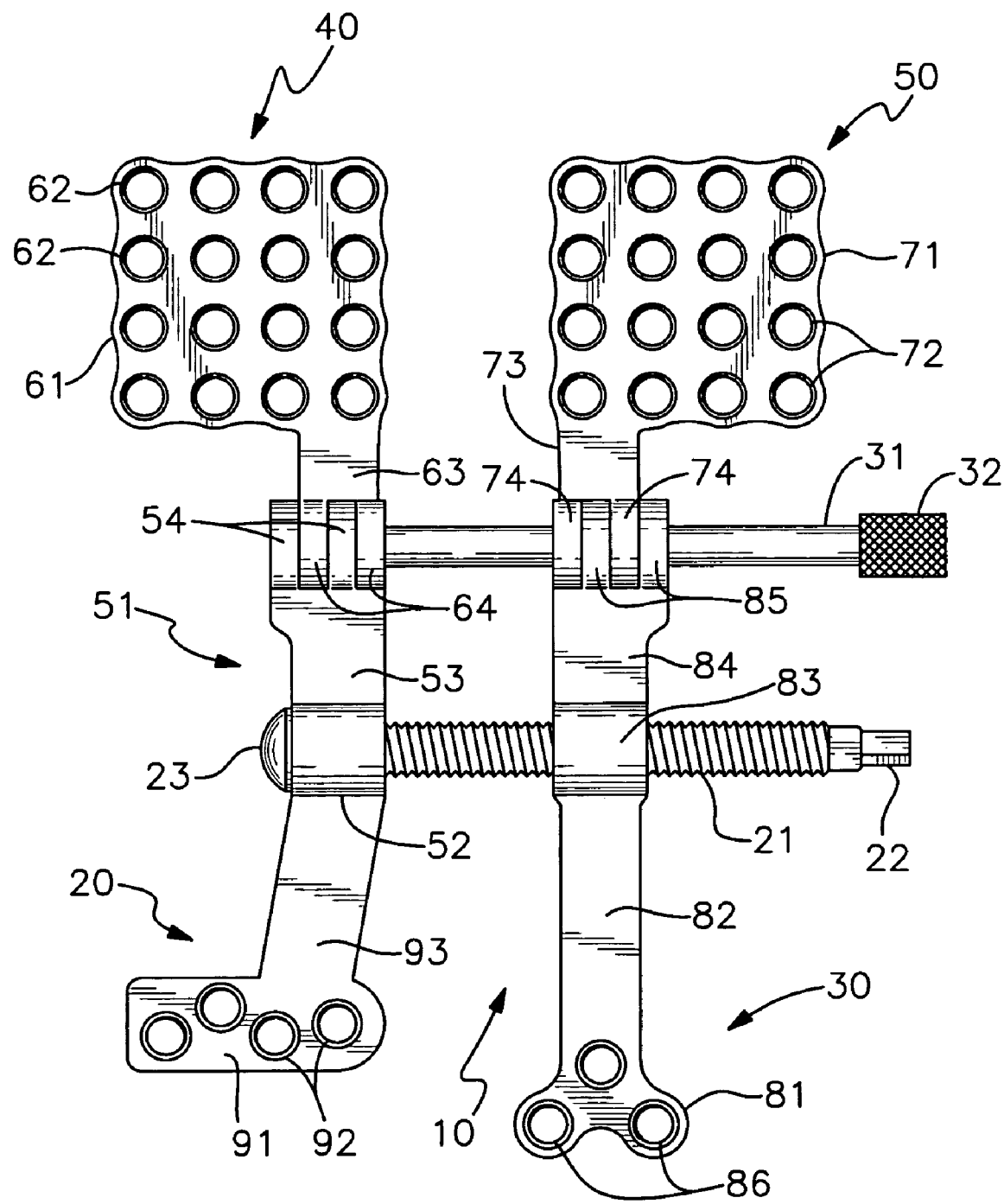
FIG. 7 is an illustration of an alternative embodiment wherein all four of the bone attachment members are bone plates.

Preferably, the threaded drive rod member 21 further comprises a drive tool engaging member 22 positioned on its anterior end, a cap member 23 to retain the drive rod member 21 in the drive rod retainer member 51, and ball post member 24 on its posterior or distal end for securing a particular embodiment of the posterior mandible attachment means 20. The posterior mandible attachment means 20 preferably comprises a ramus seat member 41 comprising flanges 42 joined to a socket 43, and a ramus bone plate 44 having bone screw apertures 45 for attachment to the ramus 103. The combination of the ball post member 24 and socket 43 comprise the swivel means 80. Alternatively, as shown in FIG. 7, the posterior mandible attachment means 20 may comprise a bone plate 91 having fastener receiving apertures 92 and mounted on an arm member 93 connected to the sleeve 52 of the drive rod retainer member 51.

The drive rod retainer member 51 comprises a non-threaded sleeve 52 to receive the drive rod member 21, a bridge plate member 53 attached to the sleeve member 52 and spaced knuckle ring members 54, the most posterior of which has internal threading 55 to receive the threaded end 33 of the releasable guide rod member 31. The anterior or proximal end of the releasable guide rod member 31 is preferably provided with a gripping portion 32 to enable easier rotation for removal.

The anterior mandible attachment means 30 preferably comprises an extended bone plate member 81, having faster-receiving apertures 86, joined to an arm 82 extending from the threaded sleeve member 83 of the bridge plate member 84, wherein the arm 82 extends from the opposite side of the threaded sleeve 83. The separation distance between the threaded sleeve member 83 and the spaced knuckle ring members 85 is equal to the distance between the sleeve member 52 and spaced knuckle ring members 54 of the drive rod retainer member 51, such that the drive rod member 21 and the releasable guide rod member 31 will lie in parallel.

FIG. 6 illustrates a representative example of how the bone distractor 10 is attached to a skull 100 having osteotomies 105 in the mandible 101 and the maxilla 102. By rotating the drive rod member 21 in the proper direction, the anterior attachment means 30 and 50, and the attached anterior segments of the mandible 101 and the maxilla 102, are moved forward relative to the posterior attachment means 20 and 40, and the posterior segments of the mandible 101 and the maxilla 102. To quickly access the interior of the mouth or throat, the releasable guide rod member 31 is unthreaded and completely removed from the drive rod retainer member 51 and the bridging plate member 84, thereby releasing and completely detaching the anterior and posterior maxilla attachment means 40 and 50, such that the jaw may be opened.

If desired, the bone distractor device 10 can be converted or utilized to distract a single bone by removing the releasable guide rod member 31, the anterior maxilla attachment means 50 and the posterior maxilla attachment means 40, leaving the distraction means 60, the anterior mandible attachment means 30 and the posterior mandible attachment means 20 operational.

It is to be understood that the bone distraction device 10 may be utilized on bones other than the combination of the mandible 101 and maxilla 102. It is further to be understood that equivalents and substitutions of certain elements set forth above may be obvious to those skilled in the art, and therefore the true scope and definition of the invention is to be as set froth in the following claims.

We claim:

1. A bone distractor device for simultaneous distraction of a mandible and a maxilla divided by osteotomies into anterior and posterior portions, the device comprising:
    posterior mandible attachment means for attachment to the posterior portion of the mandible;
    anterior mandible attachment means for attachment to the anterior portion of the mandible;
    posterior maxilla attachment means for attachment to the posterior portion of the maxilla;
    anterior maxilla attachment means for attachment to the anterior portion of the maxilla;
    distraction means to simultaneously increase the distance between the anterior mandible and anterior maxilla attachment means and the posterior mandible and posterior maxilla attachment means;
    and release means to quickly release the anterior and posterior maxilla attachment means from the anterior and posterior mandible attachment means, such that the mandible can be hinged open relative to the maxilla.

2. The distractor device of claim 1, wherein at least one of said posterior mandible attachment means, anterior mandible attachment means, posterior maxilla attachment means, and anterior maxilla attachment means comprises a bone plate.

3. The distractor device of claim 1, wherein said distractor means comprises a threaded drive rod member.

4. The distractor device of claim 3, wherein said release means comprises a guide rod member.

5. The distractor device of claim 4, wherein said threaded drive rod member and said guide rod member are disposed in parallel.

6. The distractor device of claim 1, further comprising a drive rod retainer member, a bridging plate member, a threaded drive rod member and a guide rod member, wherein said threaded drive rod member and said guide rod member are both received by said drive rod retainer member and said bridging plate member, whereby said threaded drive rod member and said guide rod member are disposed in parallel, and whereby said guide rod member is removable from said drive rod retainer member and said bridging plate member.

7. The distractor device of claim 6, wherein said anterior mandible attachment means and said anterior maxilla attachment means are joined to said bridging plate member, and wherein said posterior mandible attachment means and said posterior maxilla attachment means are joined to said drive rod retainer member.

8. The distractor device of claim 7, wherein said anterior maxilla attachment means is pivotally joined to said bridging plate member by said guide rod member and said posterior maxilla attachment means is pivotally joined to said drive rod retainer member by said guide rod member.

9. The distractor device of claim 8, wherein said anterior maxilla attachment means comprises knuckle ring members and said bridging plate member comprises knuckle ring members, said knuckle ring members being aligned to define a bore to receive said guide release rod.

10. The distractor device of claim 9, wherein said posterior maxilla attachment means comprises knuckle ring members and said drive rod retainer member comprises knuckle ring members, said knuckle ring members being aligned to define a bore to receive said guide release rod.

11. The distractor device of claim 10, wherein at least one of said knuckle ring members of said drive rod retainer member is internally threaded, and wherein said guide rod member is partially threaded, such that said guide rod member is released by unthreading said guide rod from said drive rod retainer member.

12. The distractor device of claim 6, wherein said bridging plate member comprises an internally threaded sleeve member to receive said threaded drive rod member, and wherein said drive rod retainer member comprises a non-threaded sleeve member to receive said threaded drive rod member, such that rotation of said threaded drive rod member results in increasing the separation distance between said drive rod retainer member and said bridging plate member.

13. The distractor device of claim 1, wherein said posterior mandible attachment means is joined to said distraction means by swivel means.

14. The distractor device of claim 13, said posterior mandible attachment means comprising a ramus seat member and a ramus bone plate member.

15. A bone distractor device for simultaneous distraction of a mandible and a maxilla divided by osteotomies into anterior and posterior portions, the device comprising:
   posterior mandible attachment means for attaching said device to the posterior portion of the mandible;
   anterior mandible attachment means for attaching said device to the anterior portion of the mandible;
   posterior maxilla attachment means for attaching said device to the posterior portion of the maxilla;
   anterior maxilla attachment means for attaching said device to the anterior portion of the maxilla;
   distraction means to increase the distance between the anterior mandible and anterior maxilla attachment means and the posterior mandible and posterior maxilla attachment means;
   release means to quickly release the anterior and posterior maxilla attachment means from the anterior and posterior mandible attachment means, such that the mandible can be hinged open relative to the maxilla;
   a drive rod retainer member, a bridging plate member, a threaded drive rod member and a guide rod member, wherein said threaded drive rod member and said guide rod member are both received by said drive rod retainer member and said bridging plate member, whereby said threaded drive rod member and said guide rod member are disposed in parallel, and whereby said guide rod member is removable from said drive rod retainer member and said bridging plate member;
   such that rotation of said threaded guide rod simultaneously increases the separation distance between said posterior mandible attachment means and said anterior mandible attachment means and between said posterior maxilla attachment means and said anterior maxilla attachment means.

16. The distractor device of claim 15, wherein at least one of said posterior mandible attachment means, anterior mandible attachment means, posterior maxilla attachment means, and anterior maxilla attachment means comprises a bone plate.

17. The distractor device of claim 15, wherein said threaded drive rod member and said guide rod member are disposed in parallel.

18. The distractor device of claim 15, wherein said anterior mandible attachment means and said anterior maxilla attachment means are joined to said bridging plate member, and wherein said posterior mandible attachment means and said posterior maxilla attachment means are joined to said drive rod retainer member.

19. The distractor device of claim 18, wherein said anterior maxilla attachment means is pivotally joined to said bridging plate member by said guide rod member and said posterior maxilla attachment means is pivotally joined to said drive rod retainer member by said guide rod member.

20. The distractor device of claim 19, wherein said anterior maxilla attachment means comprises knuckle ring members and said bridging plate member comprises knuckle ring members, said knuckle ring members being aligned to define a bore to receive said guide release rod.

21. The distractor device of claim 20, wherein said posterior maxilla attachment means comprises knuckle ring members and said drive rod retainer member comprises knuckle ring members, said knuckle ring members being aligned to define a bore to receive said guide release rod.

22. The distractor device of claim 21, wherein at least one of said knuckle ring members of said drive rod retainer member is internally threaded, and wherein said guide rod member is partially threaded, such that said guide rod member is released by unthreading said guide rod from said drive rod retainer member.

23. The distractor device of claim 15, wherein said bridging plate member comprises an internally threaded sleeve member to receive said threaded drive rod member, and wherein said drive rod retainer member comprises a non-threaded sleeve member to receive said threaded drive rod member, such that rotation of said threaded drive rod member results in increasing the separation distance between said drive rod retainer member and said bridging plate member.

24. The distractor device of claim 15, wherein said posterior mandible attachment means is joined to said distraction means by swivel means.

25. The distractor device of claim 24, said posterior mandible attachment means comprising a ramus seat member and a ramus bone plate member.

26. A method of simultaneously distracting a mandible and a maxilla, comprising the steps of:
    creating an osteotomy in said mandible and said maxilla to produce anterior and posterior segments of said mandible and anterior and posterior segments of said maxilla;
    providing a single distractor device having posterior mandible attachment means for attachment to the posterior segment of said mandible, anterior mandible attachment means for attachment to the anterior segment of said mandible, posterior maxilla attachment means for attachment to the posterior segment of said maxilla, anterior maxilla attachment means for attachment to the anterior segment of said maxilla, distraction means to simultaneously increase the distance between said anterior mandible and anterior maxilla attachment means and said posterior mandible and posterior maxilla attachment means, and release means to quickly release said anterior and posterior maxilla attachment means from said anterior and posterior mandible attachment means, such that said mandible can be hinged open relative to said maxilla;
    attaching said posterior mandible attachment means to the posterior segment of said mandible, attaching said anterior mandible attachment means to the anterior segment of said mandible, attaching said posterior maxilla attachment means to the posterior segment of said maxilla, and attaching said anterior maxilla attachment means to the anterior segment of said maxilla;
    and distracting said mandible and said maxilla by operating said distraction means to simultaneously increase the distance between said anterior mandible and anterior maxilla attachment means and said posterior mandible and posterior maxilla attachment means.

27. The method of claim 26, further comprising the steps of:
    allowing bone regeneration to begin within said osteotomy prior to operation of said distraction means;
    allowing bone regeneration to continue within said osteotomy after operation of said distraction means;
    and repeating the bone regeneration and distracting steps until the desired amount of distraction is achieved.

28. The method of claim 27, further comprising the steps of:
    releasing said release means to quickly release said anterior and posterior maxilla attachment means from said anterior and posterior mandible attachment means;
    and opening said mandible relative to said maxilla.

29. A method of simultaneously distracting a mandible and a maxilla, comprising the steps of:
    creating a pair of osteotomies in said mandible and said maxilla to produce an anterior segment and two posterior segments of said mandible and an anterior segment and two posterior segments of said maxilla;
    providing two distractor devices, each said distractor device having posterior mandible attachment means for attachment to a posterior segment of said mandible, anterior mandible attachment means for attachment to the anterior segment of said mandible, posterior maxilla attachment means for attachment to a posterior segment of said maxilla, anterior maxilla attachment means for attachment to the anterior segment of said maxilla, distraction means to simultaneously increase the distance between said anterior mandible and anterior maxilla attachment means and said posterior mandible and posterior maxilla attachment means, and release means to quickly release said anterior and posterior maxilla attachment means from said anterior and posterior mandible attachment means, such that said mandible can be hinged open relative to said maxilla;
    attaching, for both said distractor devices, said posterior mandible attachment means to the posterior segment of said mandible, attaching said anterior mandible attachment means to the anterior segment of said mandible, attaching said posterior maxilla attachment means to the posterior segment of said maxilla, and attaching said anterior maxilla attachment means to the anterior segment of said maxilla;
    and distracting said mandible and said maxilla by operating said distraction means to simultaneously increase the distance between said anterior mandible and said anterior maxilla attachment means and said posterior mandible and said posterior maxilla attachment means.

30. The method of claim 29, further comprising the steps of:
    allowing bone regeneration to begin within said osteotomies prior to operation of said distraction means;
    allowing bone regeneration to continue within said osteotomies after operation of said distraction means;
    and repeating the bone regeneration and distracting steps until the desired amount of distraction is achieved.

31. The method of claim 30, further comprising the steps of:
    releasing said release means to quickly release said anterior and posterior maxilla attachment means from said anterior and posterior mandible attachment means;
    and opening said mandible relative to said maxilla.

* * * * *